United States Patent [19]
Corbett

[11] Patent Number: 5,772,619
[45] Date of Patent: Jun. 30, 1998

[54] PIVOTAL BRACE FOR PROSTHESIS

[76] Inventor: Blake Corbett, 856 Lynnhaven La., La Canada, Calif. 91011

[21] Appl. No.: 791,546
[22] Filed: Jan. 31, 1997

Related U.S. Application Data

[63] Continuation of Ser. No. 418,949, Apr. 7, 1995, abandoned.
[51] Int. Cl.[6] .................................................. A61F 5/00
[52] U.S. Cl. .............................. 602/16; 602/21; 602/26
[58] Field of Search .................................. 602/5, 16, 20, 602/21, 23, 26

[56] References Cited

U.S. PATENT DOCUMENTS

| | | | |
|---|---|---|---|
| 3,708,859 | 1/1973 | Bitney | 29/430 |
| 3,902,482 | 9/1975 | Taylor | 602/16 |
| 4,088,130 | 5/1978 | Applegate | 602/16 |
| 4,353,361 | 10/1982 | Foster | 602/16 |
| 4,428,369 | 1/1984 | Peckham et al. | 602/16 |
| 4,969,452 | 11/1990 | Petrofsky et al. | 602/16 |
| 5,086,760 | 2/1992 | Neumann et al. | 602/16 X |
| 5,292,303 | 3/1994 | Bastyr et al. | 602/16 |
| 5,409,449 | 4/1995 | Nebolon | 602/16 |

*Primary Examiner*—Linda C. Dvorak
*Attorney, Agent, or Firm*—Wagner & Middlebrook

[57] ABSTRACT

A rotatable brace for a prothesis includes a pair of straps, each one connected to one of two wrapping supports secured on opposite sides of an ankle or wrist joint, a pivot joint including a pivot pin connecting the straps, a washer of polytetrafluoroethylene material interposed between the straps and surrounding the pivot pin and having a plurality of ports positioned radially outwardly of the pivot pin, with one end of one strap being of reduced width and having a semicircular end, shoulders joining the portion of reduced width with the main part of the strap, a number of threaded ports in the other of the straps axially aligned with respect to the ports in the washer, and a pair of screws passing through selected ports in the washer and threadedly engaged with the aligned threaded ports such that the brace can be rotated only until the shoulders abut against the heads of the screws. A hard impact of a shoulder against one of the screw heads causes a slight deflection of the screw within a port of the washer, permitting some resilience or "give" and reducing the impact against the pivot pin and the reduced width portion of the strap having the semicircular end.

7 Claims, 3 Drawing Sheets

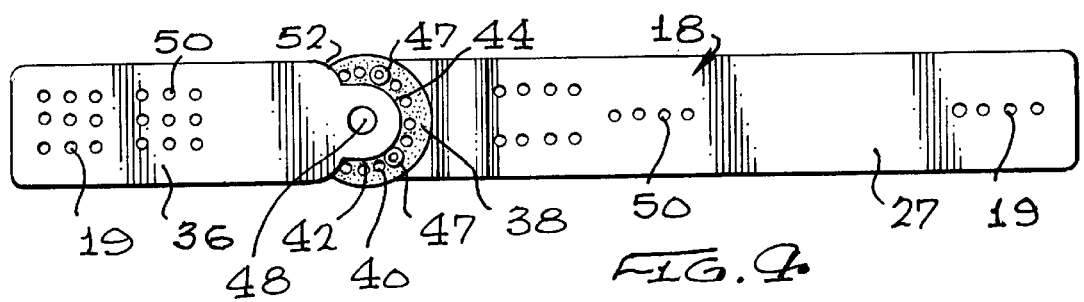
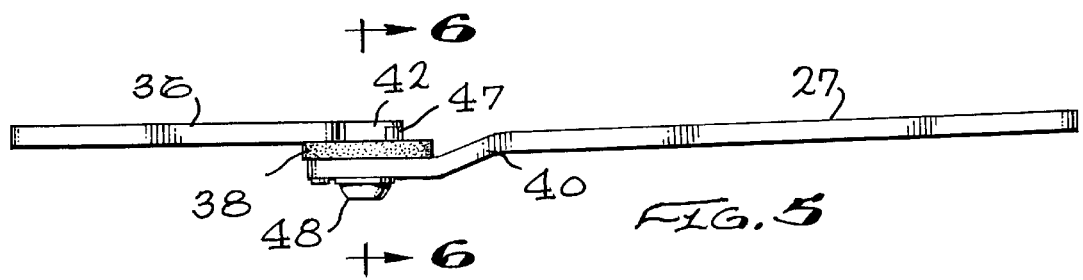
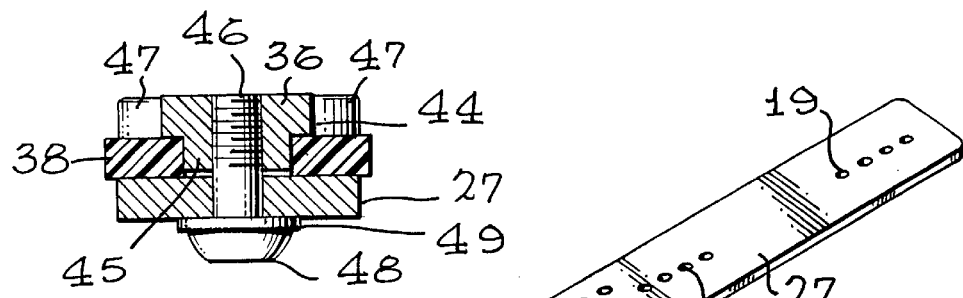
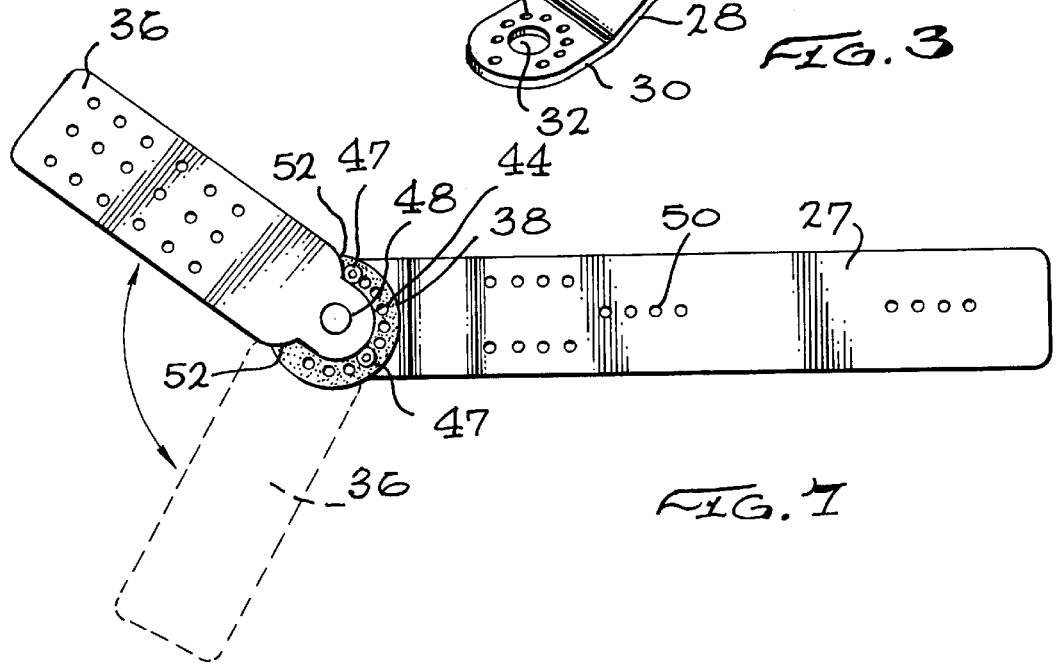

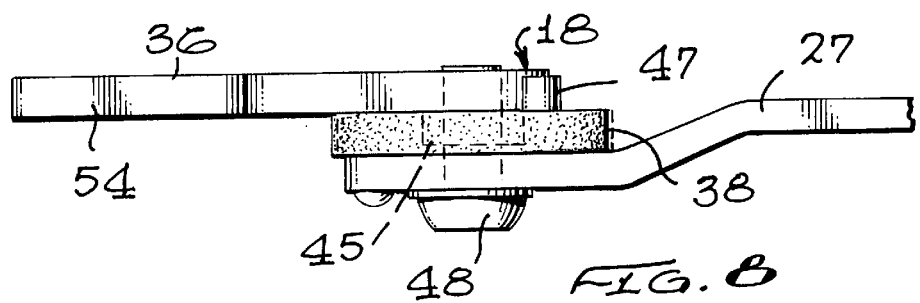
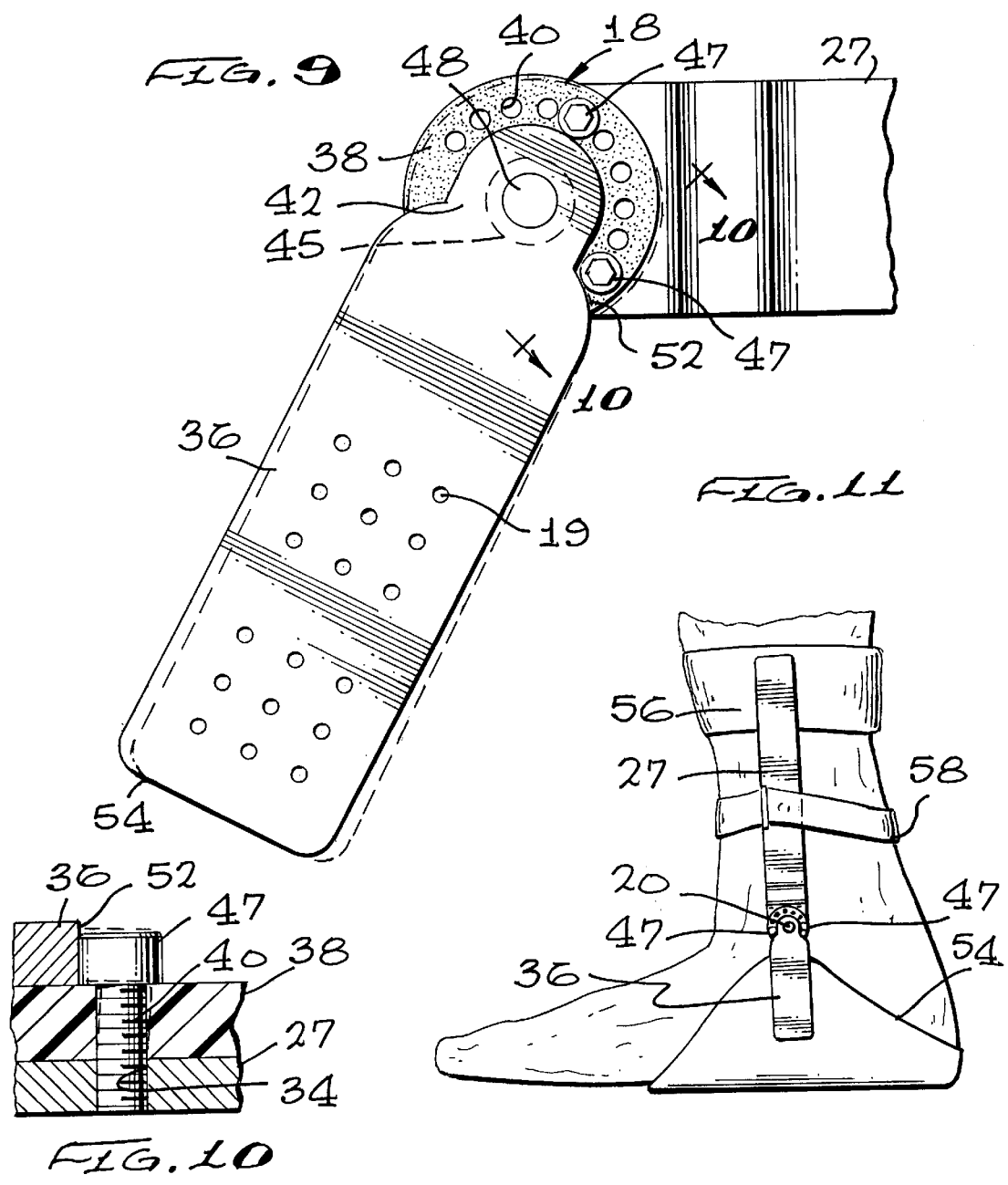

100
PIVOTAL BRACE FOR PROSTHESIS

This application is a continuation of application Ser. No. 08/418, 949 filed on Apr. 7, 1994, now abandoned

BACKGROUND OF THE INVENTION

This invention relates to prothesis in the form of braces for supporting sprained or broken joints of the human body such as wrists and ankles.

It is well known to support sprains or bone breaks near a wrist or ankle by means of supports of various kinds. Such braces may vary from wrapping a stretchable fabric strip in several layers around the joint to substantial protheses of leather or heavy fabric or metal. Frequently, it is desired that the prothesis permit a limited amount of angular movement of the joint and no more. This is often the case where the injured person wishes or needs to continue to work and it is believed that such working would not be harmful to the healing process so long as the movement of the joint adjacent the injury is limited in its amount of rotation.

Applicant was fitted with a substantial prothesis after suffering a broken wrist. The prothesis consisted of a fabric sleeve around which was secured a heavy wrapping covering a substantial part of the forearm and another heavy wrapping around the hand with a brace secured to and bridging the heavy wrappings. The brace included a pair of plastic straps attached by means of a pivot with stop members on one of the straps to limit the degree of rotation of the wrist joint. Applicant succeeded in breaking the plastic brace almost immediately, suffering some further injury in doing so. As a result, applicant sought a better brace but found that no such better brace was commercially available.

BRIEF DESCRIPTION OF THE INVENTION

A consideration of the cause of the failure of the brace led applicant to believe that the failure was due, to the fact that when the wearer applied substantial force to the brace (such as when using a hammer) at or near the time the pivot reached its maximum travel and impacted on a stop, the lateral force applied to the pivot pin became very high. This caused the pin to apply great concentrated force against the portion of the strap surrounding the pin resulting in breaking the strap. It was concluded that the principal reason for the breakage was that there was no resilience or "give" to the brace structure and that this resulted in the concentrated force described.

The brace of the invention is similar to that previously used, but incorporates a washer of TEFLON material polytetrafluoroethylene between the straps and surrounding the pivot pin. A number of threaded passages are formed in the washer aligned with similar threaded passages in one of the straps. A pair of large headed screws are secured to the washer and to the this one strap. The second strap, which is secured to the washer and the first strap by means of the threaded pivot pin, is formed with shallow threaded boss and a half-circular end of smaller width surrounding the pivot pin with the half circular end extending just beyond the pin on each side and terminating in shoulders. As the second strap is rotated around the pin, one shoulder or the other contacts the head of one of the screws which thereby serves as a stop. By placing the screws in the desired threaded passageways in the washer and the first strap, the amount of rotation permitted by the brace may be varied.

When one or the other shoulder on the second strap contacts one of the large screw heads with substantial force, the screws are deflected slightly in the direction of the force applied within the ports in the TEFLON washer, which permits a certain limited deflection of the screws. This deflection is barely discernable by one operating the brace by hand; however, it results in significant cushioning of the blow against the pivot pin. At the same time, the described structure does not permit enough deflection to significantly expand the amount of rotation initially established by the location of the screws.

BRIEF DESCRIPTION OF THE DRAWING

This invention may be more clearly understood with the following detailed description and by reference to the drawings in which:

FIG. 3 is a perspective view of one of the straps forming part of the brace shown in FIGS. 1 and 2;

FIG. 4 is a top plan view of a brace according to the invention;

FIG. 5 is a side view of the brace of FIG. 4;

FIG. 6 is an enlarged sectional view taken along line 6—6 of FIG. 5;

FIG. 7 is a top plan view of the brace of FIG. 3, showing the manner in which the rotation of the brace is limited;

FIG. 8 is an enlarged fragmentary side view of the rotated brace shown in FIG. 7;

FIG. 9 is an enlarged fragmentary top plan view of the rotated brace of FIG. 8;

FIG. 10 is a sectional view taken along line 10—10 of FIG. 9; and

FIG. 11 is a plan view of the brace of the invention used in connection with a significantly different prothesis from that of FIG. 1.

DETAILED DESCRIPTION OF THE INVENTION

Figure 1:
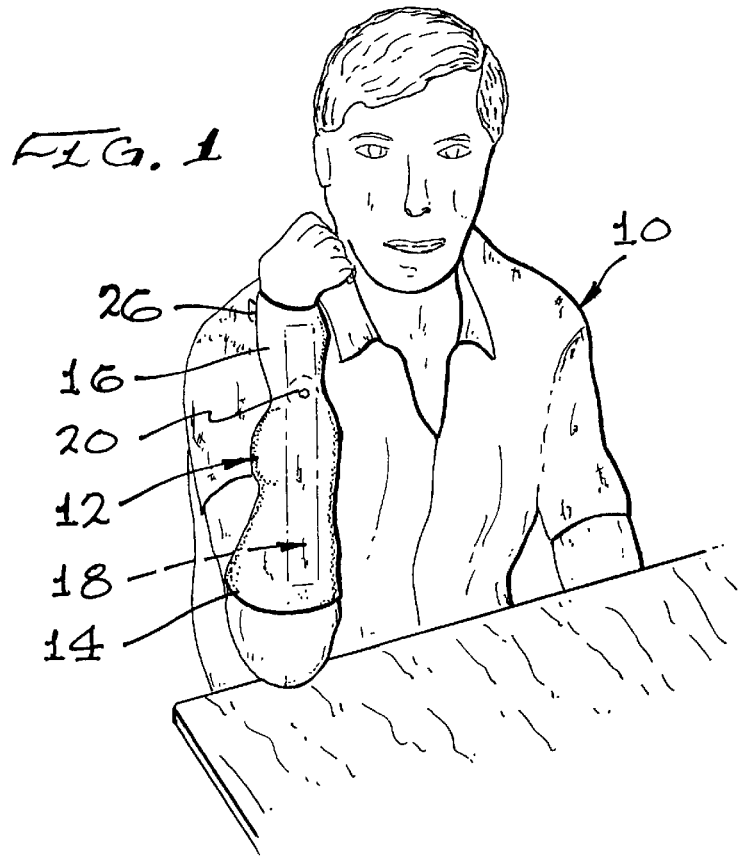
FIG. 1 is a front view of an individual wearing a prothesis and a brace according to the invention.

Referring to FIG. 1, an individual 10 is shown sitting at a table and holding an arm in such a way as to display a prothesis 12 having a brace according to the invention. The prothesis consists of a first wrapping support 14 which covers the substantial part of the wearer's forearm and a second wrapping support 16 which is wrapped around the individual's hand below the wrist. Fastened to wrapping supports 14 and 16 is a rotatable brace 18 which is secured to wrapping supports 14 and 16 in such manner to permit a desired limited rotation of the individual's wrist. Rotation is permitted around an articulated joint shown at numeral 20.

Figure 2:
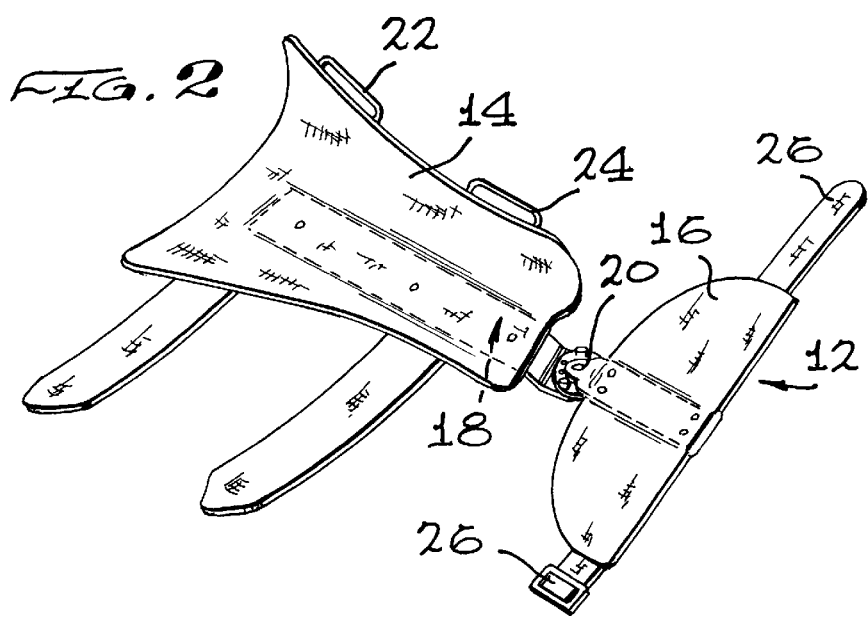
FIG. 2 is a perspective view of the prothesis of FIG. 1 shown open and unattached to an individual.

FIG. 2 is a perspective view of the prothesis of FIG. 1 shown open and unattached to an individual. It includes a forearm wrapping support 14 which includes bands and fasteners 22, 24 for fastening wrapping support 14 around the forearm of an individual as shown in FIG. 1. A hand wrapping support 16 is also shown including a band and fastener 26 for fastening wrapping support 16 around the hand of an individual. Secured to both of members 14 and 16 is an articulated brace 18 which includes a pivot structure 20 for providing a limited rotation of a wearer's wrist.

FIG. 3 is a perspective view of a strap 27 which includes a plurality of threaded ports 19 for attaching strap 27 to the wrapping support 14. It will be observed that strap 27 includes an offset 28 which sets off a pivot portion 30 which includes a centrally drilled hole 32 and a number of smaller threaded ports 34 arranged in a partial circular configuration concentrically outboard of hole 32. The depth or angle of the offset 28 is variable for different patients, and it may be formed as a ninety degree step. In some circumstances, it may be desired to place the offset on strap 36.

FIG. 4 is a top plan view of a brace according to the invention and includes strap 27 and a shorter strap 36. Interposed between straps 27 and 36 is a TEFLON polytetrafluoroethylene washer 38 which includes a series of threaded ports 40 in registry with the ports 34 of strap 27. Strap 36 includes a reduced width portion 42 terminating in a semicircular portion 44 having centered therein a boss 45 surrounding a threaded hole 46. Located in selected pairs of the ports 40 are screws 47 which pass through ports 40 and are threadedly engaged with the threaded ports 34 in strap 27. Screws 47 are removable and placed in desired pairs of ports 40 and 34 to limit rotation of the brace in accordance with the condition of the patient. A pivot pin 48 is positioned through holes 46, 32, and through the center of washer 38. A plurality of threaded holes 19 are provided in members 27 and 36 to provide for fastening the brace 20 to members 14 and 16 as desired to fit various individuals.

FIG. 5 is a side view of the brace shown in FIG. 4 and provides edge views of the straps 27 and 36 as well as washer 38. Also shown is the head of screw 47 and the semicircular portion 44 at the end of strap 36. The pivot pin 48 is shown in FIG. 5 as having a conventional bolt head; however, this member may be riveted or otherwise fastened to secure members 27, 36 and 38 together as desired. It is preferable that there be a minimum projection on the upper side of strap 36 since any such projection could contact the wearer's wrist and be uncomfortable.

FIG. 6 is an enlarged sectional view taken along line 6—6 of FIG. 5. In this view, it will be seen that the lower strap 27 is of metal (preferably aluminum or stainless steel) above which is the TEFLON washer 38 and above that the portion of strap 36 having the reduced width as shown at numeral 44. In this view, both of screws 47 are visible although partially hidden behind strap 36. The pivot pin 48 is shown and in this case, it is portrayed as a bolt threadedly engaged with member 36 including boss 45. Other suitable fastening arrangements may be made but member 36 must be free to rotate relative to member 27. The TEFLON washer 38 also provides the advantage that it permits strap 36 to move smoothly over its surface. A small TEFLON washer 49 is located under the bolt head of pivot pin 48.

FIG. 7 is a top plan view of the brace of FIG. 3 showing the manner in which rotation of the brace is limited. In this instance, it is assumed that strap 27 is held stationary and strap 36 is free to rotate around the pivot pin 48. The screws 47 are shown extending through selected threaded ports 40 in the TEFLON washer 38 and are threadedly engaged with those ports 34 of member 27 which are in registry with the chosen ports in washer 38. For those with an injury which, for a time at least, should not be rotated, there should be sets of ports 34 and 40 which cooperate with screws 47 to lock brace 20 in a non-rotatable position.

As indicated above, strap 36 has a smaller width portion 42 terminating in the semicircular contour 44. This smaller portion and the normal width of member 36 being joined by means of a pair of shoulder sections 52 as shown in FIG. 7, member 36 is free to rotate around pivot pin 48 until the shoulder section 52 strikes the head of a screw 47. Similarly, it may be rotated in the opposite direction until, as shown in dotted outline, its other shoulder makes contact with the other screw 47.

FIG. 8 is an enlarged fragmentary side view of the brace of the invention and showing one strap rotated to the limit against a stop; FIG. 9 is an enlarged fragmentary top plan view of the rotated brace of FIG. 8. It will be observed from FIG. 9 that the strap 36 is rotated to its extreme limit against the lower one of screws 47. When member 36 is forced hard against screw 46 and since a significant length of screw 46 passes through the TEFLON washer 38, the washer 38 deforms slightly and permits a small deflection of the screw 47 in the direction of the movement of shoulder 52 thereby permitting the strap 36 to rotate slightly beyond the normal stop position as shown in the dotted outline. This amount of resilience or "play" in the brace 18 substantially reduces the force on the reduced diameter portion 42 or the semicircular part 44 of strap 36 making it much less likely that this strap will break under normal or somewhat heavier than normal usage.

FIG. 10 is a sectional view taken along line 10—10 of FIG. 9. In this view, screw 47 passes through a threaded port 40 of the Teflon washer 38 and is threadedly engaged with a port 34 in strap 27. The force from shoulder 52 impinging upon the edge of the head of screw 46 causes screw 47 to be displaced slightly to the left which displacement is facilitated by the softness of the Teflon material in washer 38. This displacement, while slight, significantly reduces the concentrated force which would otherwise act on strap 36 and particularly that resulting from the force of pivot pin 48 exerted against the smaller width portion 42 and the semicircular portion 44.

FIG. 11 is a plan view of the brace of the invention used in connection with a foot and ankle prothesis significantly different from that shown in FIG. 1. In this embodiment, the strap 36 is fastened to a cup shaped foot and ankle support 54 and strap 27 is secured by means of two separate bands 56 and 58 around the leg of the wearer just above the ankle joint. Located beside the ankle joint is the pivot structure 20. As described above, the small screws 47 are adjustable to limit the rotation of the ankle joint as described.

The above described embodiments of the present invention are merely descriptive of its principles and are not to be considered limiting. The scope of the present invention instead shall be determined from the scope of the following claims including their equivalents.

What is claimed is:

1. A rotatable brace forming part of a prothesis for supporting a human joint including a first wrapping support supporting a first limb member, a second wrapping support for supporting a second limb member, said rotatable brace being secured to said wrapping supports for permitting limited rotation of said joint:

said rotatable brace comprising a first strap secured to one of said wrapping supports having a main portion and a portion of reduced width at one end terminating in a generally semicircular portion, a hole centered in said semicircular portion, and a pair of shoulder portions joining said main portion with said portion of reduced width;

a second strap secured to the other of said wrapping supports having a hole generally centered at one end thereof, and a plurality of threaded ports positioned radially outwardly of said hole;

a washer of low friction plastic material interposed between said first and second straps and having a centrally located hole and a plurality of ports aligned with said threaded ports;

a pivot pin extending through said holes in said first and second straps and through said washer; and a pair of screws having upstanding heads extending through a pair of said ports in said washer and threadedly engaged with corresponding said threaded ports, said heads limiting rotation of said brace when contacted by said shoulder portions, said screws being deflectable and said washer being deformable to absorb forces at said rotation limit to avoid damage to said brace.

2. A rotatable brace as claimed in claim 1 wherein one of said first and second straps includes an offset portion.

3. A rotatable brace as claimed in claim 1 wherein said hole in said low friction plastic member is of larger diameter than said hole in said first strap;

a boss is formed on said first strap, said hole in said first strap extends through said boss, and said boss is positioned in said larger diameter hole.

4. A rotatable brace as claimed in claim 1 wherein said low friction plastic washer is comprises a washer of polytetrafluoroethylene material.

5. A rotatable brace for a prothesis for supporting a human joint including a first wrapping support for supporting a first limb member, a second wrapping support for supporting a second limb member, said rotatable brace being secured to said wrapping supports for permitting limited rotation of said joint:

characterized in that said rotatable brace comprises a first strap secured to one of said wrapping supports having a main portion of a desired width and a portion of reduced width at one end terminating in a generally semicircular portion, a hole generally centered in said semicircular portion, a boss surrounding said hole and a pair of shoulder portions joining said reduced width portion with said main portion;

a second strap secured to the other of said wrapping supports and having an offset portion at one end defining a pivot area, a hole generally centered in said pivot area, and a plurality of threaded ports positioned concentrically radially outwardly of said hole at a radius greater than the radius of said generally semicircular portion;

a washer of low friction plastic material surrounding said boss and interposed between said first and second straps and having a plurality of ports aligned with said threaded ports;

a pivot pin extending through said holes in said first and second straps and through said washer; and a pair of screws having upstanding heads extending through a pair of said ports in said washer and threadedly engaged with selected pairs of said threaded ports, said heads limiting rotation of said brace when contacted by said shoulder portions, said screws being deflectable and said washer being deformable to absorb forces at said rotation limit to avoid damage to said brace.

6. A rotatable brace as claimed in claim 5 wherein said low friction threaded member comprises a washer of polytetrafluoroethylene material.

7. A rotatable brace as claimed in claim 5 wherein said screws are movable to selected pairs of said threaded ports to adjust the amount of rotation permitted by said brace.

* * * * *